United States Patent
McDonald

(10) Patent No.: US 8,442,649 B2
(45) Date of Patent: May 14, 2013

(54) SYSTEMS AND METHODS FOR ANCHORING LEADS OF ELECTRICAL STIMULATION SYSTEMS IN AND AROUND BONY STRUCTURES

(75) Inventor: Matthew Lee McDonald, Glendale, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 555 days.

(21) Appl. No.: 12/507,714

(22) Filed: Jul. 22, 2009

(65) Prior Publication Data
US 2011/0022101 A1      Jan. 27, 2011

(51) Int. Cl.
*A61N 1/00*      (2006.01)

(52) U.S. Cl.
USPC ............ 607/116; 607/122; 607/126; 607/127

(58) Field of Classification Search .................. 607/116, 607/122, 126–127
See application file for complete search history.

(56) References Cited

U.S. PATENT DOCUMENTS

| | | | |
|---|---|---|---|
| 5,484,445 A | 1/1996 | Knuth | |
| 6,055,456 A | 4/2000 | Gerber | |
| 6,132,456 A * | 10/2000 | Sommer et al. | 607/127 |
| 6,161,047 A | 12/2000 | King et al. | |
| 6,181,969 B1 | 1/2001 | Gord | |
| 6,292,702 B1 | 9/2001 | King et al. | |
| 6,319,241 B1 | 11/2001 | King et al. | |
| 6,360,750 B1 | 3/2002 | Gerber et al. | |
| 6,442,435 B2 | 8/2002 | King et al. | |
| 6,510,347 B2 | 1/2003 | Borkan | |
| 6,516,227 B1 | 2/2003 | Meadows et al. | |
| 6,516,231 B1 * | 2/2003 | Flammang | 607/122 |
| 6,609,029 B1 | 8/2003 | Mann et al. | |
| 6,609,032 B1 | 8/2003 | Woods et al. | |
| 6,714,822 B2 | 3/2004 | King et al. | |
| 6,741,892 B1 | 5/2004 | Meadows et al. | |
| 6,795,737 B2 | 9/2004 | Gielen et al. | |
| 6,999,819 B2 | 2/2006 | Swoyer et al. | |

(Continued)

FOREIGN PATENT DOCUMENTS

| | | |
|---|---|---|
| EP | 1048317 A2 | 11/2000 |
| EP | 1048321 A2 | 11/2000 |
| WO | 9955411 A2 | 11/1999 |
| WO | 2005062829 A2 | 7/2005 |

OTHER PUBLICATIONS

U.S. Appl. No. 11/238,240, filed Sep. 29, 2005 (20 pgs.).

*Primary Examiner* — Nicole F Lavert
(74) *Attorney, Agent, or Firm* — Frommer Lawrence & Haug LLP; Patrick R. Turner

(57) ABSTRACT

A lead assembly includes a nerve stimulation lead and at least one anchoring unit. The nerve stimulation lead includes electrodes disposed at a distal end that are electrically coupled to terminals disposed at the proximal end by a plurality of conductive wires. The at least one anchoring unit includes at least one elongated member and at least one fastener. The at least one elongated member extends along at least a portion of the nerve stimulation lead with a distal end of the at least one elongated member extending outwards from the nerve stimulation lead in proximity to the distal end of the nerve stimulation lead. The at least one fastener is attached to the distal end of the at least one elongated member and is configured and arranged for anchoring the at least one elongated member against a bony structure or against soft tissue abutting a bony structure.

12 Claims, 8 Drawing Sheets

U.S. PATENT DOCUMENTS

| | | |
|---|---|---|
| 7,191,018 B2 | 3/2007 | Gielen et al. |
| 7,244,150 B1 | 7/2007 | Brase et al. |
| 7,376,468 B2 | 5/2008 | King et al. |
| 2001/0023367 A1 | 9/2001 | King et al. |
| 2001/0025192 A1 | 9/2001 | Gerber et al. |
| 2001/0053885 A1 | 12/2001 | Gielen et al. |
| 2002/0042642 A1 | 4/2002 | Gerber |
| 2002/0151948 A1 | 10/2002 | King et al. |
| 2003/0114905 A1 | 6/2003 | Kuzma |
| 2004/0059392 A1 | 3/2004 | Parramon et al. |
| 2004/0093053 A1 | 5/2004 | Gerber et al. |
| 2004/0186543 A1 | 9/2004 | King et al. |
| 2004/0236388 A1 | 11/2004 | Gielen et al. |
| 2005/0102006 A1 | 5/2005 | Whitehurst et al. |
| 2005/0165465 A1 | 7/2005 | Pianca et al. |
| 2006/0293723 A1 | 12/2006 | Whitehurst et al. |
| 2007/0123954 A1 | 5/2007 | Gielen et al. |
| 2007/0150007 A1 | 6/2007 | Anderson et al. |
| 2007/0150036 A1 | 6/2007 | Anderson |
| 2007/0161294 A1 | 7/2007 | Brase et al. |
| 2007/0219595 A1 | 9/2007 | He |
| 2007/0239243 A1 | 10/2007 | Moffitt et al. |
| 2008/0071320 A1 | 3/2008 | Brase |
| 2008/0140169 A1* | 6/2008 | Imran ........................ 607/117 |
| 2008/0161670 A1 | 7/2008 | King et al. |
| 2008/0188917 A1 | 8/2008 | Gerber et al. |

* cited by examiner

SYSTEMS AND METHODS FOR ANCHORING LEADS OF ELECTRICAL STIMULATION SYSTEMS IN AND AROUND BONY STRUCTURES

FIELD

The present invention is directed to the area of implantable electrical stimulation systems and methods of making and using the systems. The present invention is also directed to implantable electrical stimulation leads having anchoring units configured and arranged for reducing lead migration within patients, as well as methods of making and using the leads, anchoring units, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a lead assembly includes a nerve stimulation lead and at least one anchoring unit. The nerve stimulation lead has a distal end, a proximal end, and a longitudinal length. The nerve stimulation lead includes a plurality of electrodes disposed at the distal end, a plurality of terminals disposed at the proximal end, and a plurality of conductive wires electrically coupling the plurality of electrodes to the plurality of terminals. The at least one anchoring unit includes at least one elongated member and at least one fastener. The at least one elongated member has a distal end and a proximal end and extends along at least a portion of the nerve stimulation lead with the distal end of the at least one elongated member extending outwards from the nerve stimulation lead in proximity to the distal end of the nerve stimulation lead. The at least one fastener is attached to the distal end of the at least one elongated member and is configured and arranged for anchoring the at least one elongated member against a bony structure or against soft tissue abutting a bony structure.

In another embodiment, a lead assembly includes a nerve stimulation lead and a non-conductive, porous material. The nerve stimulation lead has a distal end, a proximal end, an outer surface, and a longitudinal length. The nerve stimulation lead includes a plurality of electrodes disposed at the distal end, a plurality of terminals disposed at the proximal end, and a plurality of conductive wires electrically coupling the plurality of electrodes electrically to the plurality of terminals. The non-conductive, porous material is permanently disposed over at least a portion of the outer surface of the nerve stimulation lead such that at least a portion of the porous material is disposed over at least one of the electrodes. The porous material is configured and arranged to promote adhesion of patient tissue to the porous material to anchor the nerve stimulation lead to patient tissue. The porous material is configured and arranged such that electrical stimulation energy transmits through the porous material.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads having anchoring units configured and arranged for reducing lead migration within patients, as well as methods of making and using the leads, anchoring units, and electrical stimulation systems.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent applications Ser. Nos. 10/353,101, 10/503,281, 11/238,240; 11/319,291; 11/327,880; 11/375,638; 11/393,991; and 11/396,309, all of which are incorporated by reference.

Figure 1:
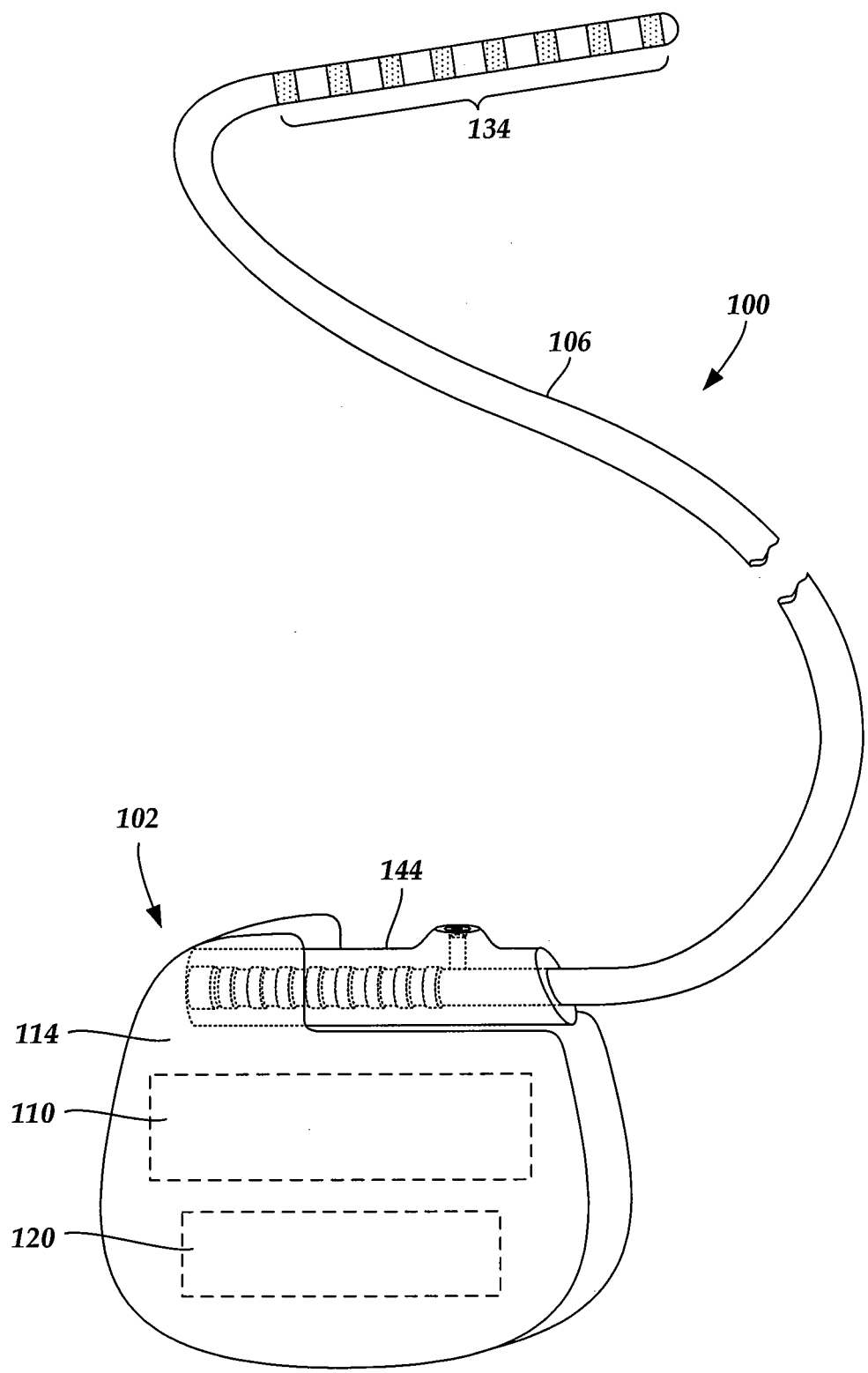
FIG. 1 is a schematic view of one embodiment of an electrical stimulation system, according to the invention.

FIG. 1 illustrates schematically one embodiment of an electrical stimulation system 100. The electrical stimulation system includes a control module (e.g., a stimulator or pulse generator) 102 and at least one lead 106 coupled to the control module 102. Each lead 106 typically includes an array of electrodes 134. The control module 102 typically includes an electronic subassembly 110 and an optional power source 120 disposed in a sealed housing 114. The control module 102 typically includes a connector 144 (FIG. 2A, see also 222 and 250 of FIG. 2B) into which the proximal end of the one or more leads 106 can be plugged to make an electrical connection via conductive contacts on the control module 102 and terminals (e.g., 210 in FIG. 2A and 236 of FIG. 2B) on each of the one or more leads 106. In at least some embodiments, a lead is isodiametric along a longitudinal length of the lead 106. In addition, one or more lead extensions 224 (see FIG. 2B) can be disposed between the one or more leads 106 and the control module 102 to extend the distance between the one or more leads 106 and the control module 102 of the embodiment shown in FIG. 1.

The electrical stimulation system or components of the electrical stimulation system, including one or more of the leads 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of one or more leads 106 are typically disposed in, or separated by, a non-conductive, biocompatible material such as, for example, silicone, polyurethane, polyetheretherketone ("PEEK"), epoxy, and the like or combinations thereof. The leads 106 may be formed in the desired shape by any process including, for example, molding (including injection molding), casting, and the like. The non-conductive material typically extends from the distal end of the one or more leads 106 to the proximal end of each of the one or more leads 106.

Terminals (e.g., 210 in FIG. 2A and 236 of FIG. 2B) are typically disposed at the proximal end of the one or more leads 106 of the electrical stimulation system 100 for connection to corresponding conductive contacts (e.g., 214 in FIG. 2A and 240 of FIG. 2B) in connectors (e.g., 144 in FIGS. 1-2A and 222 and 250 of FIG. 2B) disposed on, for example, the control module 102 (or to conductive contacts on a lead extension, an operating room cable, or an adaptor). Conductor wires (not shown) extend from the terminals (e.g., 210 in FIG. 2A and 236 of FIG. 2B) to the electrodes 134. Typically, one or more electrodes 134 are electrically coupled to a terminal (e.g., 210 in FIG. 2A and 236 of FIG. 2B). In at least some embodiments, each terminal (e.g., 210 in FIG. 2A and 236 of FIG. 2B) is only connected to one electrode 134. The conductor wires may be embedded in the non-conductive material of the lead 106 or can be disposed in one or more lumens (not shown) extending along the lead 106. In some embodiments, there is an individual lumen for each conductor wire. In other embodiments, two or more conductor wires may extend through a lumen. There may also be one or more lumens (not shown) that open at, or near, the proximal end of the lead 106, for example, for inserting a stylet rod to facilitate placement of the lead 106 within a body of a patient. Additionally, there may also be one or more lumens (not shown) that open at, or near, the distal end of the lead 106, for example, for infusion of drugs or medication into the site of implantation of the one or more leads 106. In at least one embodiment, the one or more lumens may be flushed continually, or on a regular basis, with saline, epidural fluid, or the like. In at least some embodiments, the one or more lumens can be permanently or removably sealable at the distal end.

Figure 2A:
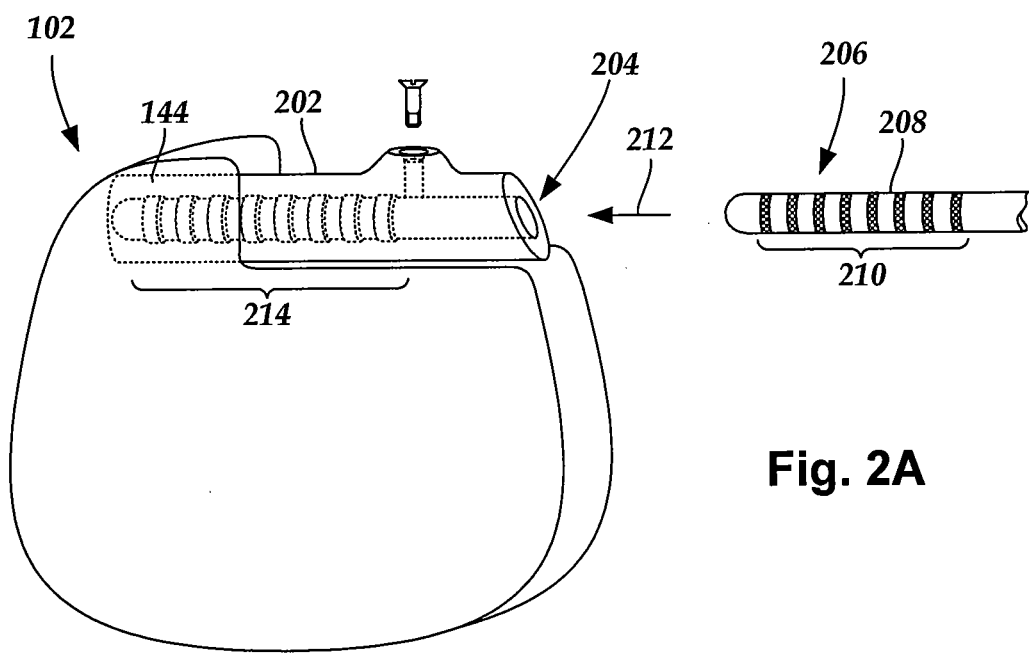
FIG. 2A is a schematic view of one embodiment of a proximal portion of a lead and a control module of an electrical stimulation system, according to the invention.

In at least some embodiments, leads are coupled to connectors disposed on control modules. In FIG. 2A, a lead 208 is shown configured and arranged for insertion to the control module 102. The connector 144 includes a connector housing 202. The connector housing 202 defines at least one port 204 into which a proximal end 206 of a lead 208 with terminals 210 can be inserted, as shown by directional arrow 212. The connector housing 202 also includes a plurality of conductive contacts 214 for each port 204. When the lead 208 is inserted into the port 204, the conductive contacts 214 can be aligned with the terminals 210 on the lead 208 to electrically couple the control module 102 to the electrodes (134 of FIG. 1) disposed at a distal end of the lead 208. Examples of connectors in control modules are found in, for example, U.S. Pat.

No. 7,244,150 and U.S. patent application Ser. No. 11/532, 844, which are incorporated by reference.

Figure 2B:
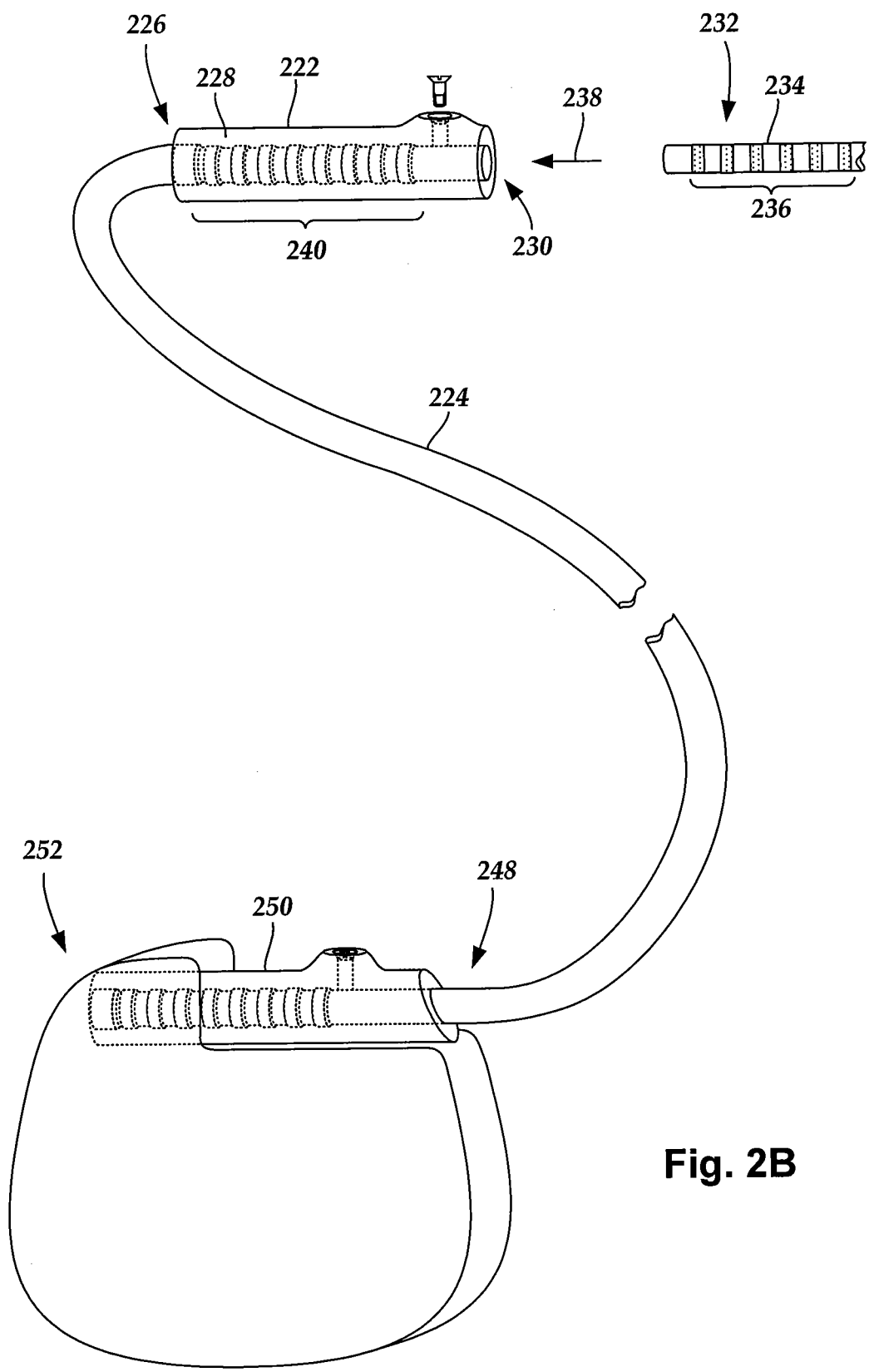
FIG. 2B is a schematic view of one embodiment of a proximal portion of a lead and a lead extension of an electrical stimulation system, according to the invention.

In FIG. 2B, a connector 222 is disposed on a lead extension 224. The connector 222 is shown disposed at a distal end 226 of the lead extension 224. The connector 222 includes a connector housing 228. The connector housing 228 defines at least one port 230 into which a proximal end 232 of a lead 234 with terminals 236 can be inserted, as shown by directional arrow 238. The connector housing 228 also includes a plurality of conductive contacts 240. When the lead 234 is inserted into the port 230, the conductive contacts 240 disposed in the connector housing 228 can be aligned with the terminals 236 on the lead 234 to electrically couple the lead extension 224 to the electrodes (134 of FIG. 1) disposed at a distal end (not shown) of the lead 234.

In at least some embodiments, the proximal end of a lead extension is similarly configured and arranged as a proximal end of a lead. The lead extension 224 may include a plurality of conductive wires (not shown) that electrically couple the conductive contacts 240 to a proximal end 248 of the lead extension 224 that is opposite to the distal end 226. In at least some embodiments, the conductive wires disposed in the lead extension 224 can be electrically coupled to a plurality of terminals (not shown) disposed on the proximal end 248 of the lead extension 224. In at least some embodiments, the proximal end 248 of the lead extension 224 is configured and arranged for insertion into a connector disposed in another lead extension. In other embodiments, the proximal end 248 of the lead extension 224 is configured and arranged for insertion into a connector disposed in a control module. As an example, in FIG. 2B the proximal end 248 of the lead extension 224 is inserted into a connector 250 disposed in a control module 252.

Sometimes leads are used to stimulate nerves that extend through foramina of bony structures, such as sacra. Sometimes leads are used to stimulate nerves that extend around, or in proximity to, bony structures, such as sacra. Nerves disposed in and around the sacrum are sometimes stimulated to treat one or more different types of ailments, including fecal incontinence, urge incontinence, interstitial cystitis, chronic pelvic pain, and urine retention. Sacral nerves can extend through one or more foramen of a sacrum. It will be understood that leads can also be used to stimulate nerves that extend through, or in proximity to, other bony structures, such as one or more vertebrae superior to the sacrum.

Figure 3:
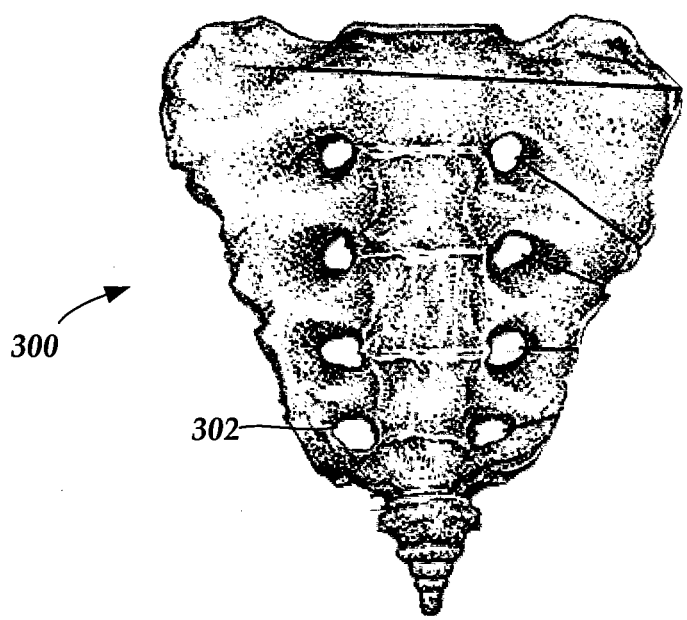
FIG. 3 is a schematic front view of one embodiment of a sacrum that includes foramina through which sacral nerves may extend, according to the invention.

Implantable electrical stimulation systems can sometimes be used for nerve stimulation and tissue stimulation, in general, including, for example, sacral nerve stimulation. One way an electrical stimulation system can be implanted for sacral nerve stimulation is to position a distal end of a lead in or around one or more sacral foramina through which a desired sacral nerve extends. FIG. 3 is a schematic front view of one embodiment of a sacrum 300. The sacrum 300 includes a plurality of foramina, such as foramen 302. Anchoring leads on or around a bony structure, such as sacrum 300, may be difficult due to patient movement occasionally causing anchored leads to dislodge. Previously, some leads have been used that incorporate one or more tines disposed on a lead proximal to the plurality of electrodes. However, such tines may not provide adequate anchoring ability and may not allow a lead to be optimally positioned for stimulation. Additionally, when a distal end of a lead extends through a foramen, one or more proximally-disposed tines may not prevent the migration of the distal end of the lead back through the foramen.

Anchoring units are described for use with implantable electrical stimulation systems for anchoring leads at target stimulation sites (e.g., sacral nerves (or other nerves) in proximity to a sacrum (or other bony structure)). In at least some embodiments, anchoring units are configured and arranged for anchoring on or around foramina of bony structures. For example, in some embodiments, the anchoring units may be used to anchor leads to sacra for use during sacral nerve stimulation. In at least some embodiments, anchoring units are configured and arranged for anchoring a lead to the walls of a foramen of a bony structure through which the lead extends. In at least some embodiments, anchoring units are configured and arranged for anchoring a lead to regions of a bony structure in proximity to one or more foramina. In at least some embodiments, anchoring units are configured and arranged for anchoring a lead to a region of a bony structure that is not in proximity to a foramen. In alternate embodiments, the anchoring units can also anchor to other features on bony structures, such as grooves, fissures, cracks, and indentations in the bony structure. It will also be understood that these anchoring techniques can also be used to anchor a lead to soft tissue. For example, these anchoring techniques can also be used to anchor a lead to soft tissue on either side of a foramen, or in another location that is not in proximity to a foramen.

In at least some embodiments, an anchoring unit includes at least one fastener coupled to a distal end of at least one elongated member coupleable to a lead. In at least some embodiments, the anchoring unit includes a material disposed over at least a portion of an outer surface of the lead that promotes adhesion of patient tissue to the material. The anchoring unit can be disposed anywhere along a longitudinal length of the lead. For example, the anchoring unit can be disposed proximal to electrodes (e.g., electrodes 134 of FIG. 1) disposed at a distal end of the lead, between two adjacent electrodes, or distal to the electrodes. In some embodiments, the anchoring unit is removably coupled to the lead. In other embodiments, the anchoring unit is permanently coupled to the lead. In at least some embodiments, a plurality of anchoring units can be used to anchor the lead at a target stimulation site within a patient.

In at least some embodiments, the anchoring unit includes an elongated member and a fastener. Any type of biocompatible fastener (e.g., one or more screws, suturable strings or wires, staples, hooks, or the like) can be used to fasten the anchoring unit to a bony structure or to soft tissue. In at least some embodiments, the fasteners can be unfastened from a bony structure or soft tissue without damaging the anchoring unit. In at least some embodiments, the anchoring unit may include a plurality of elongated members. In at least some embodiments, the anchoring unit may include a plurality of fasteners.

Figure 4A:
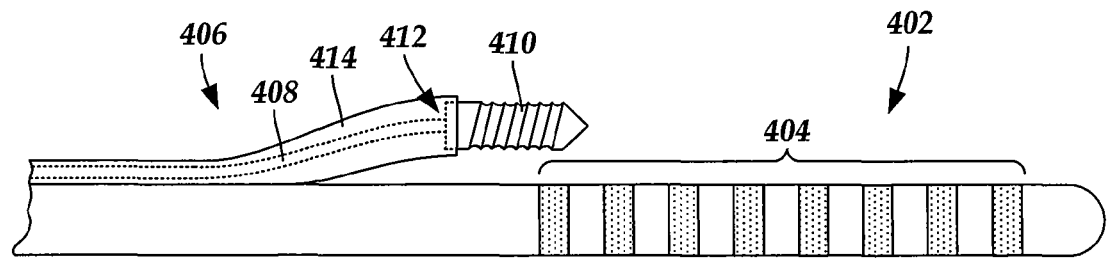
FIG. 4A is a schematic side view of one embodiment of an anchoring unit coupled to a distal end of a lead, the anchoring unit including an elongated member and a fastener, according to the invention.

FIG. 4A is a schematic side view of one embodiment of a distal end of a lead 402. A plurality of electrodes 404 are disposed on the distal end of the lead 402. An anchoring unit 406 is coupled to the lead 402. In FIG. 4A the anchoring unit 406 is shown disposed proximal to the electrodes 404. As discussed above, however, the anchoring unit 406 may be disposed anywhere along a longitudinal length of the lead 402. The anchoring unit 406 includes an elongated member 408 and a fastener 410 coupled to the elongated member 408.

In at least some embodiments, the fastener 410 is a rotary device (e.g., a screw, drill bit, corkscrew, or the like) configured and arranged to rotatably couple to a bony structure. In at least some embodiments, the elongated member 408 is a drive element with a proximal end (not shown) and a distal end 412. In at least some embodiments, the distal end 412 of the elongated member 408 is coupled to the fastener 410. In at least some embodiments, the elongated member 408 is configured and arranged to rotate the fastener 410. In at least some embodiments, the rotation of the fastener 410 can be used to couple the fastener 410 to (or uncouple the fastener 410 from) a bony structure. In at least some embodiments, the proximal end of the elongated member 408 is coupled to a motor (not shown) configured and arranged for providing power to rotate the elongated member 408. In at least some embodiments, the elongated member 408 can be manually rotated. In at least some embodiments, the elongated member 408 is removably coupled to the motor.

In at least some embodiments, the elongated member 408 is disposed in a sheath 414. In at least some embodiments, at least a portion of the sheath 414 extends along a longitudinal length of the lead 402. In some embodiments, the sheath 414 is removably coupled to the lead 402. In other embodiments, the sheath 414 is permanently coupled to the lead 402. In at least some embodiments, the sheath 414 has a distal end that is in proximity to the distal end of the lead 402. In at least some embodiments, the distal end of the sheath 414 is not coupled to the lead 410. In at least some embodiments, the distal end of the sheath 414 extends outward from the lead 402 such that the fastener 410 is positioned in proximity to the lead 402. In at least some embodiments, the sheath 414 is rigid or semi-rigid. In at least some embodiments, the distal end of the sheath 414 can be moved such that the fastener 410 can be moved longitudinally or laterally with respect to the lead 402.

In at least some embodiments, the lead 402 defines a port that extends through an outer surface of the lead 402 to an inner region of the lead 402 beneath the outer surface (see e.g., port 614 of FIG. 6). In at least some embodiments, the elongated member 408 extends within at least a portion of the lead 402 proximal to the port and the distal end of the elongated member 408 extends outward from the port.

Figure 4B:
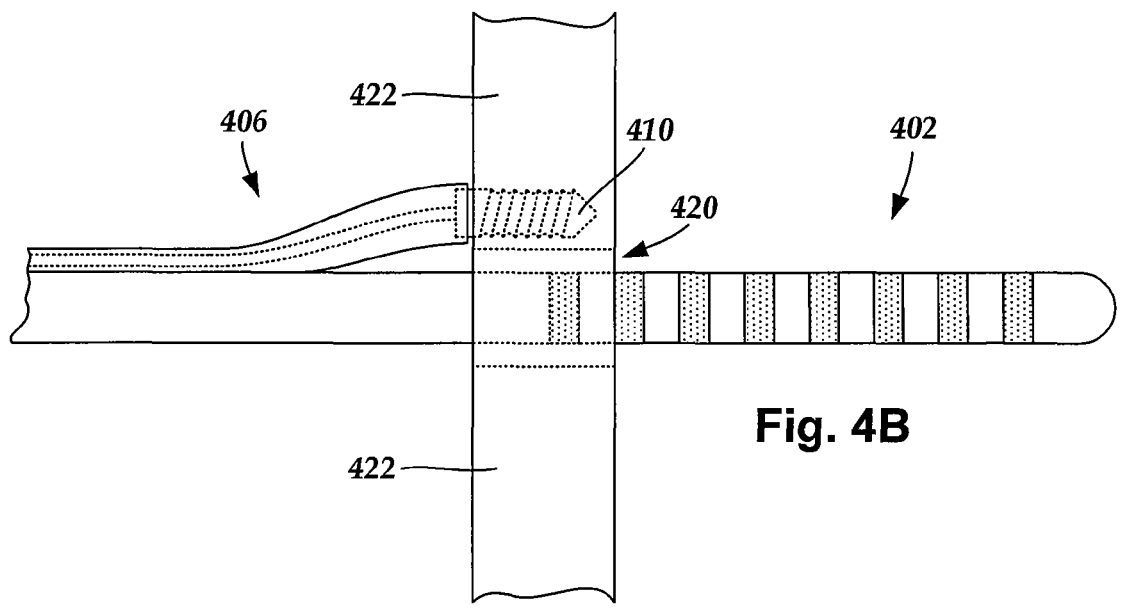
FIG. 4B is a schematic side view of one embodiment of the anchoring unit and distal end of the lead of FIG. 4A, the lead extending into a foramen of a bony structure and the anchoring unit coupled to the bony structure in proximity to the foramen, according to the invention.

In at least some embodiments, the anchoring unit 406 is configured and arranged to retain the lead 402 in or around a foramen of a bony structure. FIG. 4B is a schematic side view of one embodiment of the distal end of the lead 402 extending into a foramen 420 of a bony structure 422. The anchoring unit 406 is coupled to the bony structure 422 in proximity to the foramen 420. In at least some embodiments, implantation of the lead 410 can be facilitated by rotating the fastener 410 in a first direction to couple the fastener 410 to the bony structure 422. In at least some embodiments, explantation of the lead 402 can be facilitated by rotating the fastener 410 in a second direction that is opposite from the first direction. In at least some embodiments, explantation of the lead 402 can be facilitated by uncoupling the anchoring unit 406 from the lead 402, either with or without rotating the fastener 410 in the second direction.

Figure 5:
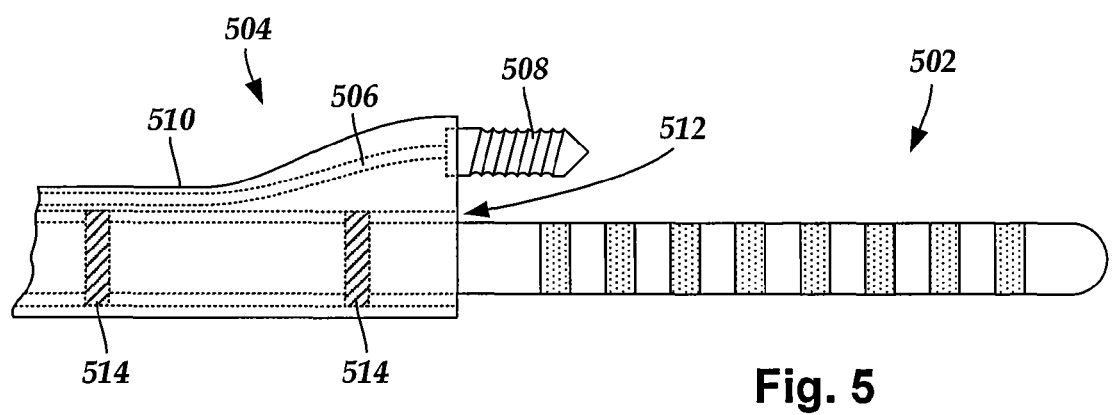
FIG. 5 is a schematic side view of another embodiment of an anchoring unit coupled to a distal end of a lead, the anchoring unit including an elongated member and a fastener disposed in a sleeve coupled to the lead, according to the invention.

In at least some embodiments, the anchoring unit includes a sleeve coupled to the lead. FIG. 5 is a schematic side view of another embodiment of a distal end of a lead 502 and an anchoring unit 504 coupled to the lead 502. The anchoring unit 504 includes an elongated member 506 and a fastener 508 disposed in a sleeve 510. In at least some embodiments, the fastener 508 is a rotary device (e.g., a screw, drill bit, corkscrew, or the like) configured and arranged to rotatably couple to a bony structure. In at least some embodiments, the elongated member 506 is a drive element configured and arranged to rotate the fastener 410. It will be understood that the anchoring unit 504 may be disposed anywhere along a longitudinal length of the lead 502.

In at least some embodiments, the sleeve 510 defines a lumen 512 configured and arranged to receive at least a portion of the lead 502. In at least some embodiments, the sleeve 510 is removably coupled to the lead 502 by one or more couplers 514. For example, in at least some embodiments, one or more of the couplers 514 could be a set screw element. In at least some embodiments, one or more of the couplers 514 could be attached using sutures in the same manner that suture sleeves are currently sutured to leads (e.g., a suture could be placed around the exterior of a sleeve to attach it to the underlying lead). In at least some embodiments, the lumen 512 of the sleeve 510 forms an interference fit with the lead 502. In at least some embodiments, the sleeve 510 is permanently coupled to the lead 502 via the one or more couplers 514 (e.g., adhesive or the like).

In at least some embodiments, the lead 502 can be anchored to a bony structure, such as the bony structure 422 in (FIG. 4B). In at least some embodiments, the lead 502 can be implanted by anchoring the sleeve 510 to the bony structure, via the fastener 508. Once the sleeve 510 is anchored, the lead 502 can be extended through the lumen 512 of the sleeve 510 and positioned at a target stimulation site (e.g., sacral nerves (or other nerves) in proximity to a sacrum (or other bony structure)) in proximity to the anchoring site. In at least some embodiments, once the lead 502 has been extended through the lumen 512 of the sleeve 510 to the target stimulation site, the lead 502 can be coupled to the sleeve (e.g., via an interference fit, via the one or more couplers 514, or the like), either removably or permanently.

Figure 6A:
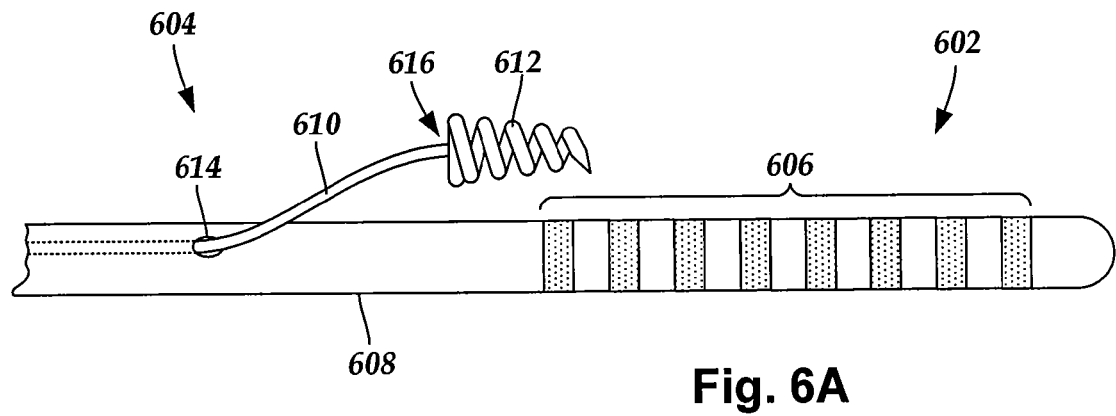
FIG. 6A is a schematic side view of yet another embodiment of an anchoring unit coupled to a distal end of a lead, the anchoring unit including an elongated member and a fastener, according to the invention.

In at least some embodiments, the anchoring unit includes a guide wire extending along a longitudinal length of a lead. FIG. 6A is a schematic side view of yet another embodiment of a distal end of a lead 602 and an anchoring unit 604 for anchoring the lead 602 at a target stimulation site within a patient. The lead 602 includes electrodes 606 and an outer surface 608. The anchoring unit 604 includes an elongated member 610 and a fastener 612. In at least some embodiments, the lead 602 defines a port 614 that extends through the outer surface 608 of the lead 602 to an inner region of the lead 602 beneath the outer surface 608. In at least some embodiments, the elongated member 610 is a guide wire with a proximal end (not shown) and a distal end 616. In at least some embodiments, the fastener 612 is coupled to the distal end 616 of the elongated member 610. It will be understood that the anchoring unit 604 may be disposed anywhere along a longitudinal length of the lead 602.

Figure 6B:
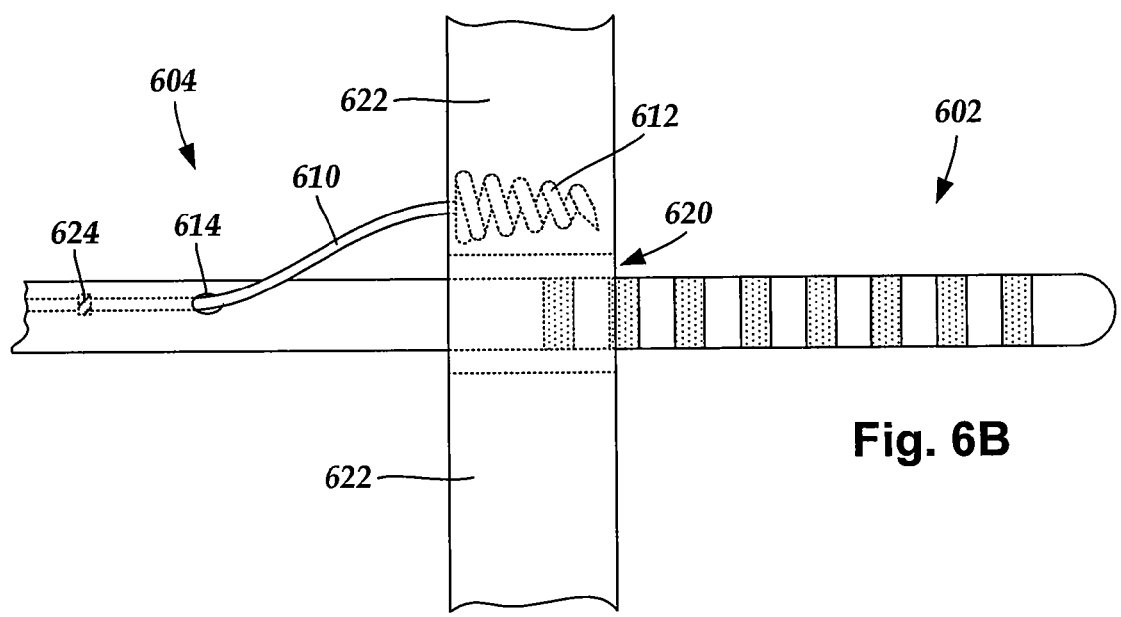
FIG. 6B is a schematic side view of one embodiment of the anchoring unit and distal end of the lead of FIG. 6A, the lead extending into a foramen of a bony structure and the anchoring unit coupled to the bony structure in proximity to the foramen, according to the invention.

In at least some embodiments, the anchoring unit 604 is configured and arranged to retain the lead 602 in or around a foramen of a bony structure. FIG. 6B is a schematic side view of one embodiment of the distal end of the lead 602 and anchoring unit 604. The lead 602 extends into a foramen 620 of a bony structure 622. The anchoring unit 604 is coupled to the bony structure 622 in proximity to the foramen 620.

In at least some embodiments, the elongated member 610 can be inserted into a patient and the fastener 612 can be anchored to the bony structure 622 in proximity to a target stimulation site (e.g., sacral nerves (or other nerves) in proximity to a sacrum (or other bony structure)). The proximal end of the elongated member 610 can be inserted into the port 614 and extended beneath the outer surface 608. The elongated member 610 can then be used to guide the lead 602 to the target stimulation site. For example, the lead 602 can be slid along a longitudinal length of the elongated member 610. In at least some embodiments, one or more other devices may be used to facilitate guidance of the lead 602 along the elongated member 610, such as a stylet. In at least some embodiments, once the lead 602 has been guided along the elongated member 610 to the target stimulation site, the elongated member 610 can be coupled to the lead 602 (e.g., via an interference fit, via the one or more couplers 624, or the like), either removably or permanently, thereby anchoring the lead 602 at the target stimulation site.

In at least some embodiments, the anchoring unit includes a coating of porous material that can be disposed over one or more portions of an outer surface of a lead and that promotes adhesion of patient tissue to the porous material, thereby anchoring the lead to the patient tissue. In at least some embodiments, the porous material is disposed, at least in part, over at least a portion of at least one of the electrodes (e.g., electrodes 134 of FIG. 1) disposed on the lead. In at least some embodiments, the porous material is permanently disposed on the lead. In at least some embodiments, the porous material is disposed on the lead for the life of the lead. In at least some embodiments, the porous material is disposed on the lead for the expected life of the lead. In at least some embodiments, the porous material is disposed on the lead for the expected implanted life of the lead within a patient.

In at least some embodiments, the porous material is formed as one or more jackets or membranes. In at least some embodiments, the one or more jackets of porous material are slidably disposed over one or more portions of the lead. In at least some embodiments, the porous material promotes tissue ingrowth without being sticky to materials other than patient tissue.

Figure 7A:
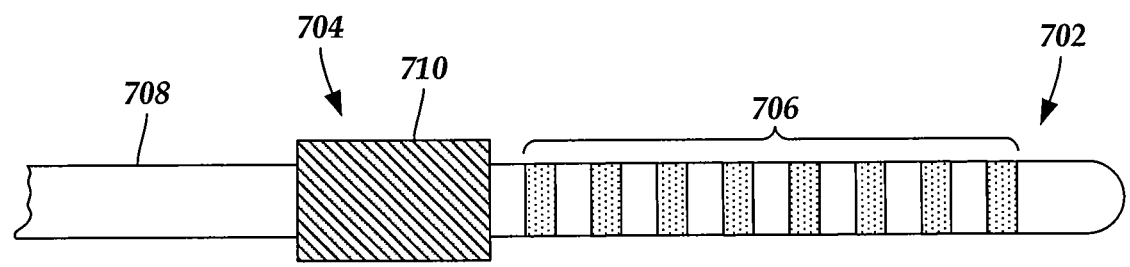
FIG. 7A is a schematic side view of another embodiment of an anchoring unit coupled to a distal end of a lead with electrodes, the anchoring unit including a coating of a porous material disposed over a portion of an outer surface of the lead proximal to the electrodes, according to the invention.

FIG. 7A is a schematic side view of one embodiment of a distal end of a lead 702 and an anchoring unit 704 for anchoring the lead 702 at a target stimulation site within a patient. The lead 702 includes electrodes 706 and an outer surface 708. The anchoring unit 704 includes a coating of porous material 710 disposed over at least a portion of an outer surface 708 of the lead 702 proximal to the electrodes 706.

The porous material 710 may be any biocompatible material suitable for applying to the outer surface 708 of the lead 702 and configured and arranged for promoting adhesion of patient tissue, or tissue in-growth, to the porous material 710 (e.g., polytetrafluoroethylene, expanded polytetrafluoroethylene, or the like). In at least some embodiments, the porous material 710 is formed from one or more materials having pores that are sized to promote adhesion of patient tissue to the porous material 710. In at least some embodiments, the pore sizes are of uniform dimension. In at least some embodiments, the pores have a diameter of up to 0.001 inches (approximately 0.003 cm). In at least some embodiments, the pores have a diameter of up to 0.002 inches (approximately 0.005 cm). In at least some embodiments, the pores have a diameter of up to 0.003 inches (approximately 0.008 cm).

In at least some embodiments, the pores of the porous material 710 have a density that promotes adhesion of patient tissue to the porous material 710. In at least some embodiments, the pore density is at least 50% of the open surface area. In at least some embodiments, the pore density is at least 55% of the open surface area. In at least some embodiments, the pore density is at least 60% of the open surface area. In at least some embodiments, the pore density is at least 65% of the open surface area. In at least some embodiments, the pore density is at least 70% of the open surface area. In at least some embodiments, the pore density is at least 75% of the open surface area.

Figure 7B:
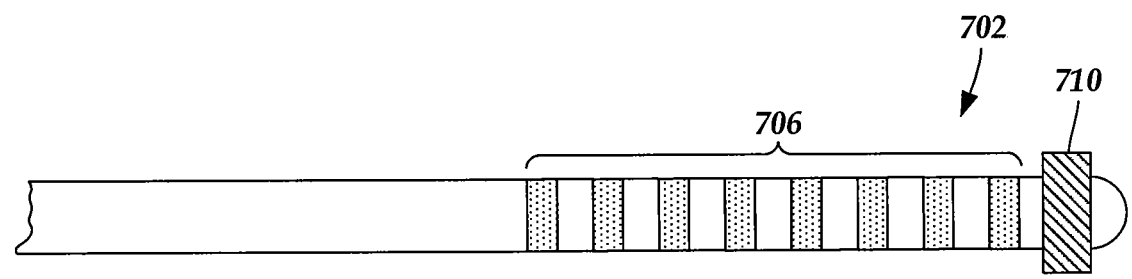
FIG. 7B is a schematic side view of one embodiment of the anchoring unit and distal end of the lead of FIG. 7A, the porous material disposed distal to the electrodes, according to the invention.

In at least some embodiments, the porous material 710 is disposed, at least in part, over a portion of the lead 702 that is distal to the electrodes 706. FIG. 7B is a schematic side view of one embodiment of the distal end of the lead 702. In FIG. 7B, the porous material 710 is shown disposed over a portion of the lead 702 that is distal to the electrodes 706.

Figure 7C:
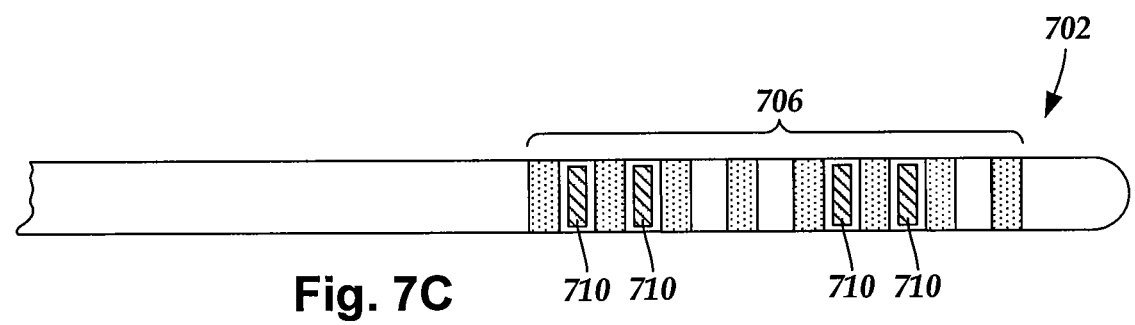
FIG. 7C is a schematic side view of one embodiment of the anchoring unit and distal end of the lead of FIG. 7A, the porous material disposed between adjacent electrodes, according to the invention.

In at least some embodiments, the porous material 710 is disposed, at least in part, over a portion of the lead 702 that is between two adjacent electrodes 706. In at least some embodiments, the porous material 710 is disposed over a plurality of discrete portions of the lead 702. For example, in at least some embodiments, the porous material 710 is disposed between two or more adjacent pairs of the electrodes 706. FIG. 7C is a schematic side view of one embodiment of the distal end of the lead 702. In FIG. 7C, the porous material 710 is shown disposed over portions of the lead 702 between several adjacent pairs of the electrodes 706.

Figure 7D:
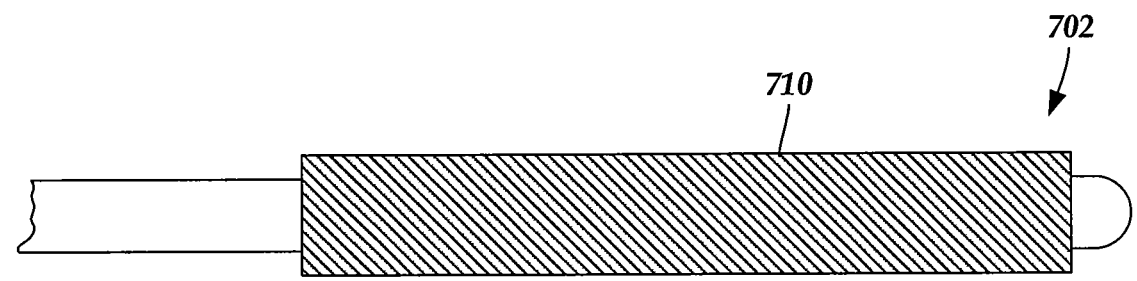
FIG. 7D is a schematic side view of one embodiment of the anchoring unit and distal end of the lead of FIG. 7A, the porous material disposed over the electrodes, according to the invention.

In at least some embodiments, the porous material 710 is disposed, at least in part, over at least a portion of one or more of the electrodes 706. In at least some embodiments, the porous material 710 is configured and arranged such that electrical energy from the electrodes 706 can be transmitted through the porous material 710. In at least some embodiments, the pore size of the porous material 710 is selected to allow transmission of electrical energy through the porous material 710 when the porous material 710 is disposed over at least a portion of one or more of the electrodes 706. FIG. 7D is a schematic side view of one embodiment of the distal end of the lead 702. In FIG. 7D, the porous material 710 is shown disposed over a portion of the lead 702 such that at least a portion of the porous material 710 is disposed over each of the electrodes 706.

Figure 7E:
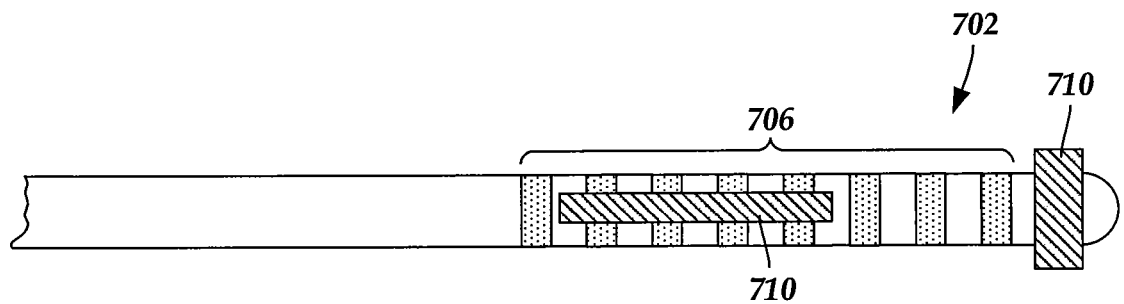
FIG. 7E is a schematic side view of one embodiment of the anchoring unit and distal end of the lead of FIG. 7A, some of the porous material disposed over some of the electrodes and some of the porous material disposed distal to the electrodes, according to the invention.

It will be understood that the porous material 710 can be disposed over two or more discrete portions of the lead 702 anywhere along a longitudinal length of the lead 702. For example, in at least some embodiments, the porous material 710 is disposed over at least some of the electrodes 706 and also over a portion of the lead 702 distal to the electrodes 706. FIG. 7E is a schematic side view of one embodiment of the distal end of the lead 702. In FIG. 7E, some of the porous material 710 is shown disposed over some of the electrodes 706 and some of the porous material 710 is shown disposed over a portion of the lead 702 that is distal to the electrodes 706.

In at least some embodiments, the anchoring unit 704 is configured and arranged to retain the lead 702 at a target stimulation site in or around a foramen of a bony structure. In at least some embodiments, the porous material 710 is positioned such that, when the lead 702 is positioned at the target stimulation site, the porous material 710 is disposed over one or more portions of the lead 702 that are in proximity to patient tissue to which the lead 702 can be anchored, such as a surface of the bony structure 722 or walls of the foramen 720.

Figure 7F:
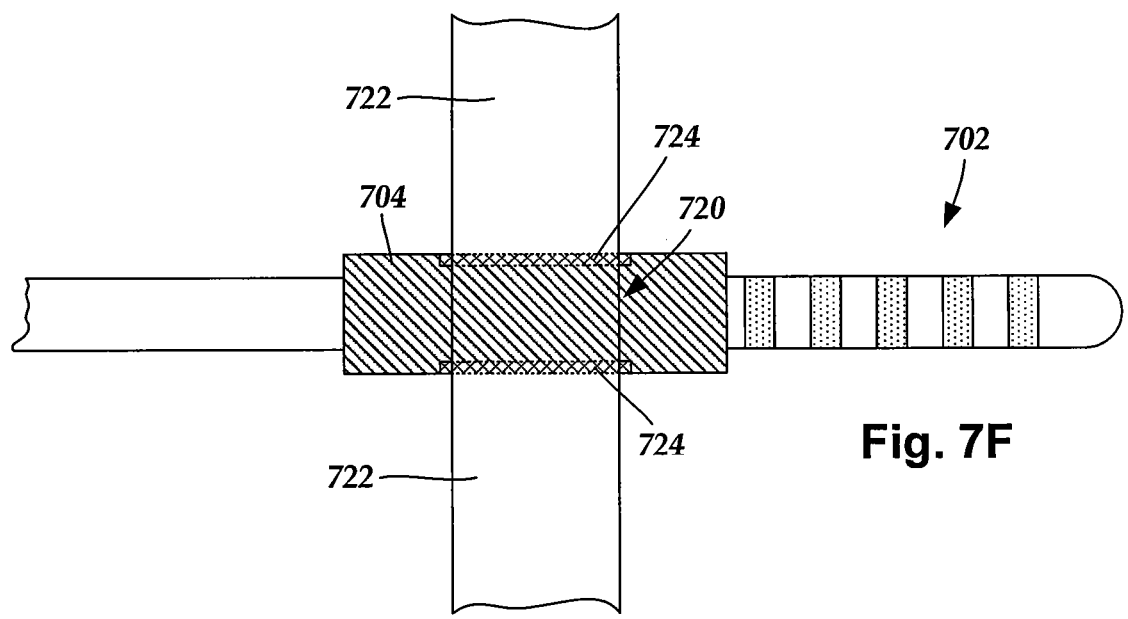
FIG. 7F is a schematic side view of one embodiment of the anchoring unit and distal end of the lead of FIG. 7A, the lead extending into a foramen of a bony structure and the anchoring unit coupled to walls of the foramen via patient tissue extending from the walls and adhering to the porous material, according to the invention.

FIG. 7F is a schematic side view of one embodiment of the distal end of the lead 702 extending into a foramen 720 of a bony structure 722. The porous material 710 is disposed over a portion of the lead 702 that includes the proximal-most electrodes 706 and a portion of the lead 702 that is proximal to the electrodes 706. The porous material 710 is in proximity to at least one surface of the foramen 720, such as one or more walls of the foramen 720. In FIG. 7F, patient tissue 724 attached to walls of the foramen 720 is shown adhered to the porous material 710, thereby retaining the lead 702 to the walls of the foramen 720.

In at least some embodiments, the porous material 710 is used with one or more other anchoring units, such as one or more of the anchoring units shown in FIGS. 4-6B. In at least some embodiments, the porous material 710 is used with a temporary anchoring system for temporarily anchoring the lead 702 to patient tissue upon implantation until enough patient tissue adheres to the porous material 710 to anchor the lead 702 to patient tissue. The temporary anchoring system may be any biocompatible anchoring system formed for temporary use. In at least some embodiments, the temporary anchoring system can be explanted. In at least some embodiments, the temporary anchoring system includes one or more fasteners (e.g., clips, hooks, sutures, or the like) formed from one or more resorbable materials. In at least some embodiments, the period of resorption of the one or more resorbable materials is substantially less than the expected life of the lead 702. In at least some embodiments, the period of resorption of the one or more resorbable materials is substantially less than the expected life of the lead. In at least some embodiments, the period of resorption of the one or more resorbable materials is substantially less than the expected implanted life of the lead 702 within a patient.

Figure 8:
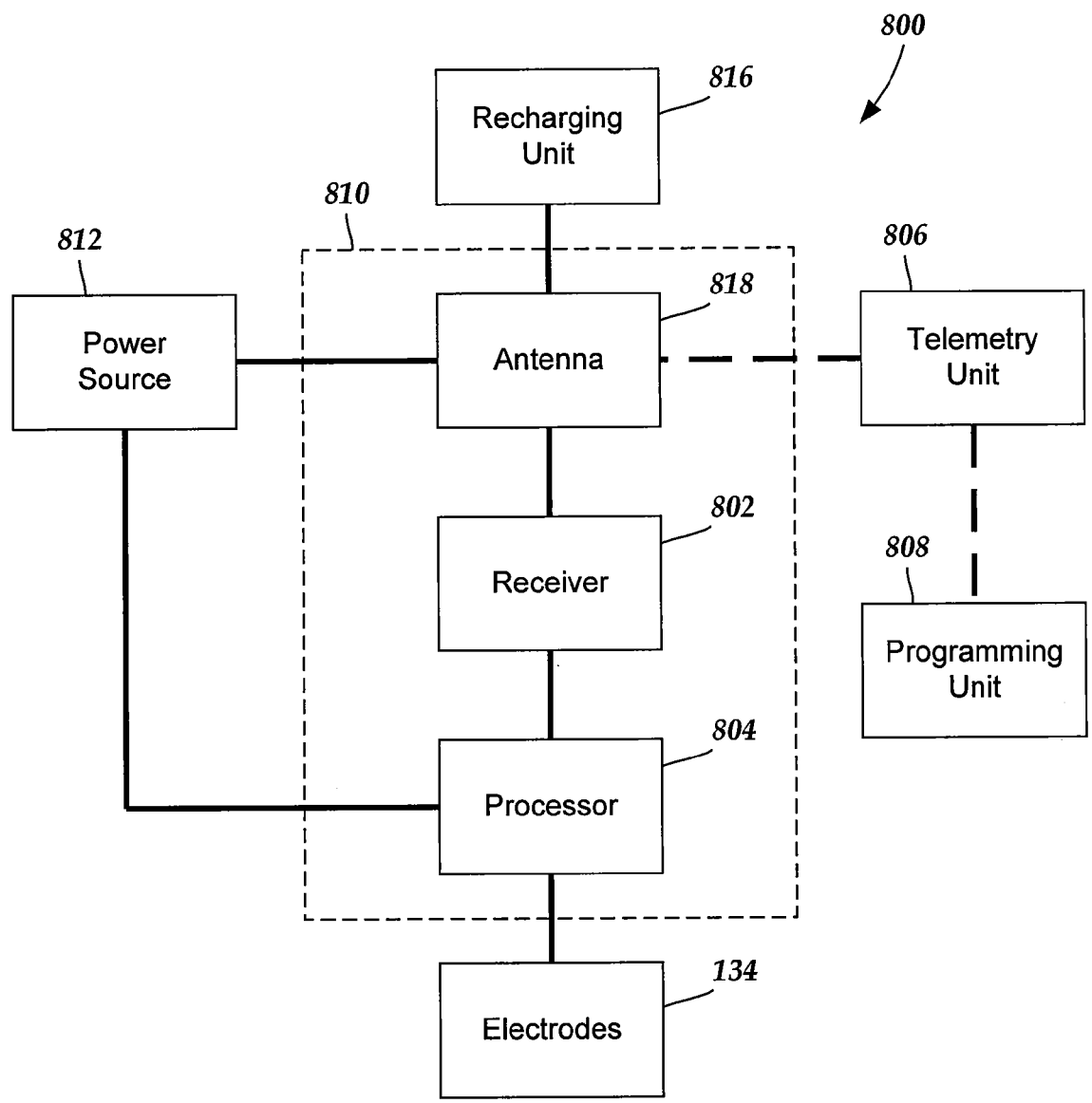
FIG. 8 is a schematic overview of one embodiment of components of a stimulation system, including an electronic subassembly disposed within a control module, according to the invention.

FIG. 8 is a schematic overview of one embodiment of components of an electrical stimulation system 800 including an electronic subassembly 810 disposed within a control module. It will be understood that the electrical stimulation system can include more, fewer, or different components and can have a variety of different configurations including those configurations disclosed in the stimulator references cited herein.

Some of the components (for example, power source 812, antenna 818, receiver 802, and processor 804) of the electrical stimulation system can be positioned on one or more circuit boards or similar carriers within a sealed housing of an implantable pulse generator, if desired. Any power source 812 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 818 or a secondary antenna. The external power source can be in a device that is mounted on the skin of the user or in a unit that is provided near the user on a permanent or periodic basis.

If the power source 812 is a rechargeable battery, the battery may be recharged using the optional antenna 818, if desired. Power can be provided to the battery for recharging by inductively coupling the battery through the antenna to a recharging unit 816 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 804 is generally included to control the timing and electrical characteristics of the electrical stimulation system. For example, the processor 804 can, if desired, control one or more of the timing, frequency, strength, duration, and waveform of the pulses. In addition, the processor 804 can select which electrodes can be used to provide stimulation, if desired. In some embodiments, the processor 804 may select which electrode(s) are cathodes and which electrode(s) are anodes. In some embodiments, the processor 804 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 808 that, for example, allows modification of pulse characteristics. In the illustrated embodiment, the processor 804 is coupled to a receiver 802 which, in turn, is coupled to the optional antenna 818. This allows the processor 804 to receive instructions from an external source to, for example, direct the pulse characteristics and the selection of electrodes, if desired.

In one embodiment, the antenna 818 is capable of receiving signals (e.g., RF signals) from an external telemetry unit 806 which is programmed by a programming unit 808. The programming unit 808 can be external to, or part of, the telemetry unit 806. The telemetry unit 806 can be a device that is worn on the skin of the user or can be carried by the user and can have a form similar to a pager, cellular phone, or remote control, if desired. As another alternative, the telemetry unit 806 may not be worn or carried by the user but may only be available at a home station or at a clinician's office. The programming unit 808 can be any unit that can provide information to the telemetry unit 806 for transmission to the electrical stimulation system 800. The programming unit 808 can be part of the telemetry unit 806 or can provide signals or information to the telemetry unit 806 via a wireless or wired connection. One example of a suitable programming unit is a computer operated by the user or clinician to send signals to the telemetry unit 806.

The signals sent to the processor 804 via the antenna 818 and receiver 802 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 800 to cease operation, to start operation, to start charging the battery, or to stop charging the battery. In other embodiments, the stimulation system does not include an antenna 818 or receiver 802 and the processor 804 operates as programmed.

Optionally, the electrical stimulation system 800 may include a transmitter (not shown) coupled to the processor 804 and the antenna 818 for transmitting signals back to the telemetry unit 806 or another unit capable of receiving the signals. For example, the electrical stimulation system 800 may transmit signals indicating whether the electrical stimulation system 800 is operating properly or not or indicating when the battery needs to be charged or the level of charge remaining in the battery. The processor 804 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A lead assembly comprising:
   a nerve stimulation lead with a distal end, a proximal end, an outer surface, and a longitudinal length, the nerve stimulation lead comprising:
      a plurality of electrodes disposed at the distal end of the nerve stimulation lead,
      a plurality of terminals disposed along the proximal end of the nerve stimulation lead,
      at least one port defined in the outer layer proximal to the plurality of electrodes, and
      a plurality of conductive wires electrically coupling the plurality of electrodes to the plurality of terminals; and at least one anchoring unit configured and arranged for anchoring the nerve stimulation lead against a bony structure or against soft tissue abutting a bony structure and for remaining permanently coupled to the nerve stimulation lead while the nerve stimulation lead is anchored against the bony structure or against soft tissue abutting the bony structure, the at least one anchoring unit comprising at least one elongated member having a distal end and a proximal end, the at least one elongated member extending along at least a portion of the nerve stimulation lead beneath the outer layer of the nerve stimulation lead with the distal end of the at least one elongated member extending outwards from the port, wherein the portion of the nerve stimulation lead along which the at least one elongated member extends beneath the outer layer of the nerve stimulation lead is proximal to the port, and at least one fastener attached to the distal end of the at least one elongated member, the at least one fastener configured and arranged for anchoring the at least one elongated member against a bony structure or against soft tissue abutting a bony structure.

2. The lead assembly of claim 1, wherein the at least one elongated member comprises a drive element.

3. The lead assembly of claim 1, wherein the at least one fastener is a rotary device configured and arranged for anchoring the at least one elongated member against a bony structure or against soft tissue by rotation of the at least one fastener.

4. The lead assembly of claim 1, wherein the at least one elongated member is removably coupled to the nerve stimulation lead.

5. The lead assembly of claim 1, wherein the at least one elongated member is disposed in a sheath coupled to the nerve stimulation lead.

6. The lead assembly of claim 5, wherein the sheath is permanently coupled to the nerve stimulation lead.

7. The lead assembly of claim 5, wherein the sheath is removably coupled to the nerve stimulation lead.

8. The lead assembly of claim 1, wherein the at least one elongated member comprises a guide wire.

9. The lead assembly of claim 1, wherein the at least one fastener comprises at least one of a pin, a staple, a screw, or a suturable wire.

10. An electrical stimulating system comprising:
the lead assembly of claim 1; and
a control module configured and arranged to electrically couple to the proximal end of the nerve stimulation lead, the control module comprising
a housing, and
an electronic subassembly disposed in the housing; and
a connector for receiving the nerve stimulation lead of the lead assembly, the connector having a proximal end and a distal end, the connector comprising
a connector housing defining a port at the distal end of the connector, the port configured and arranged for receiving the proximal end of the nerve stimulation lead, of the lead assembly, and
a plurality of connector contacts disposed in the connector housing, the connector contacts configured and arranged to couple to at least one of the plurality of terminals disposed on the proximal end of the nerve stimulation lead of the lead assembly.

11. The lead assembly of claim 1, wherein the at least one fastener is configured and arranged for anchoring the at least one elongated member against a bony structure or against soft tissue abutting a bony structure with the at least one fastener aligned along the longitudinal length of the neurostimulation lead with a portion of the neurostimulation lead that is distal to the port and proximal to the plurality of electrodes.

12. The lead assembly of claim 1, wherein the at least one fastener is configured and arranged for anchoring the at least one elongated member against a bony structure or against soft tissue abutting a bony structure with the at least one fastener aligned along the longitudinal length of the neurostimulation lead with the plurality of electrodes.

* * * * *